US010973684B2

(12) United States Patent
Bischoff et al.

(10) Patent No.: US 10,973,684 B2
(45) Date of Patent: Apr. 13, 2021

(54) MACHINING DEVICE AND METHOD

(71) Applicant: Carl Zeiss Meditec AG, Jena (DE)

(72) Inventors: Mark Bischoff, Jena (DE); Dirk Muehlhoff, Jena (DE); Gregor Stobrawa, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 218 days.

(21) Appl. No.: 16/233,869

(22) Filed: Dec. 27, 2018

(65) Prior Publication Data

US 2019/0201237 A1 Jul. 4, 2019

Related U.S. Application Data

(60) Continuation of application No. 14/990,270, filed on Jan. 7, 2016, now Pat. No. 10,195,082, which is a
(Continued)

(30) Foreign Application Priority Data

Mar. 23, 2004 (DE) ...................... 10 2004 014 181.9

(51) Int. Cl.
*B23K 26/06* (2014.01)
*A61F 9/008* (2006.01)
(Continued)

(52) U.S. Cl.
CPC .............. *A61F 9/008* (2013.01); *A61F 9/007* (2013.01); *A61F 9/00827* (2013.01);
(Continued)

(58) Field of Classification Search
CPC ...... A61F 9/007; A61F 9/008; A61F 9/00827; A61F 2009/00872; H01S 3/0007;
(Continued)

(56) References Cited

U.S. PATENT DOCUMENTS 4,826,299 A 5/1989 Powell
5,219,343 A 6/1993 L'Esperance, Jr.
(Continued)

FOREIGN PATENT DOCUMENTS

EP 0 257 836 A1 3/1988
EP 0 764 858 A2 3/1997
(Continued)

OTHER PUBLICATIONS

Dorn, "The focus of light—linear polarization breaks the rotational symmetry of the focal spot," J. of Modern Optics, 2003, vol. 50, No. 12, pp. 1917-1926.
(Continued)

*Primary Examiner* — Hung D Nguyen
(74) *Attorney, Agent, or Firm* — Patterson Thuente Pedersen, P.A.

(57) ABSTRACT

The aim of the invention is to machine a material by application of non-linear radiation. The aim is achieved by modifying the laser radiation emitted by a laser beam source with the aid of a polarization modulator in such a way that laser radiation focused into the material is polarized in a linear fashion, the direction of polarization varying across the cross section of the beam.

32 Claims, 6 Drawing Sheets

Related U.S. Application Data division of application No. 10/593,501, filed as application No. PCT/EP2005/003066 on Mar. 22, 2005, now Pat. No. 9,254,222.

(51) Int. Cl.

| | | |
|---|---|---|
| A61F 9/007 | (2006.01) | |
| B23K 26/38 | (2014.01) | |
| G02B 27/09 | (2006.01) | |
| G02F 1/35 | (2006.01) | |
| H01S 3/00 | (2006.01) | |
| H01S 3/13 | (2006.01) | |
| B23K 26/16 | (2006.01) | |
| B23K 26/00 | (2014.01) | |

(52) U.S. Cl.
CPC .......... B23K 26/38 (2013.01); G02B 27/0927 (2013.01); G02F 1/3523 (2013.01); H01S 3/0007 (2013.01); H01S 3/0071 (2013.01); H01S 3/1308 (2013.01); *A61F 2009/00872* (2013.01)

(58) Field of Classification Search
CPC ..... H01S 3/0071; H01S 3/1308; B23K 26/38; G02B 27/0927; G02F 1/3523
USPC .............. 219/121.6, 121.61, 121.72, 121.73, 219/121.67, 121.68, 121.69, 1, 21.78, 219/121.79; 606/4, 5, 6, 10, 11
See application file for complete search history.

(56) References Cited

U.S. PATENT DOCUMENTS

| | | | |
|---|---|---|---|
| 5,470,329 A | 11/1995 | Sumiya | |
| 5,782,822 A * | 7/1998 | Telfair | A61F 9/008 606/10 |
| 5,984,916 A | 11/1999 | Lai | |
| 6,086,204 A | 7/2000 | Magnante | |
| 6,110,166 A | 8/2000 | Juhasz | |
| 6,191,880 B1 | 2/2001 | Schuster | |
| 6,268,586 B1 | 7/2001 | Stuart et al. | |
| 6,325,792 B1 | 12/2001 | Swinger et al. | |
| 6,381,259 B2 | 4/2002 | Cordingley et al. | |
| 6,497,701 B2 | 12/2002 | Shimmick et al. | |
| 6,555,781 B2 | 4/2003 | Ngoi et al. | |
| 6,755,819 B1 | 6/2004 | Waelti | |
| 6,932,807 B1 | 8/2005 | Tomita et al. | |
| 7,503,916 B2 * | 3/2009 | Shimmick | A61B 3/1005 606/10 |
| RE46,493 E * | 8/2017 | Lin | A61F 9/008 |
| 2001/0016733 A1 | 8/2001 | Frey et al. | |
| 2002/0125230 A1 | 9/2002 | Haight et al. | |
| 2003/0078753 A1 | 4/2003 | Campin et al. | |
| 2004/0087118 A1 | 5/2004 | Maegawa et al. | |
| 2004/0124184 A1 | 7/2004 | An et al. | |
| 2004/0155017 A1 * | 8/2004 | Hunt | B23K 26/361 219/121.69 |
| 2004/0196469 A1 | 10/2004 | Wang et al. | |

FOREIGN PATENT DOCUMENTS

| | | |
|---|---|---|
| EP | 1 279 386 A1 | 1/2003 |
| WO | WO 93.25166 A1 | 12/1993 |
| WO | WO 01/11408 A1 | 2/2001 |
| WO | WO 03/028940 A1 | 4/2003 |

OTHER PUBLICATIONS

Helseth, "Roles of polarization, phase and amplitude in solid immersion lens systems," Optics Communications, 2001, vol. 191, pp. 161-172.
Homepage "optics.org", http://optics.org/articles/news/9/11/20/1.
Koenig et al., "Intratissue surgery with 80 MHz nanojoule femtosecond laser pulses in the near infrared", Optics Express, 2002, vol. 10, No. 3, pp. 171-176.
Korte et al., "Towards nanostructuring with femtosecond laser pulses", Appl. Phys. A, 2003, vol. 77, pp. 229-235.
Niziev, "peculiarities of laser cutting with polarized radiation," SPIE, 1999, vol. 688, pp. 169-178.
Niziev, "Influence of beam polarization on laser cutting efficiency," J. Phys. D.: Appl. Phys., 1999, vol. 32, pp. 1455-1461.
Quabis, "Focusing light to a tighter spot," Optics Communications, 2000, vol. 179, pp. 1-7.
Quabis, "Reduction of the spot size by using a radially polarized laser beam," Proc. SPIE, 2001, vol. 4429, pp. 105-111.
Zhan, "Focus shaping using cylindrical vector beams," Optics Express, 2002, vol. 10, No. 7, pp. 324,331.
Application and File History for U.S. Appl. No. 10/593,501, filed Sep. 20, 2006. Inventors: Bischoff et al.
Application and File History for U.S. Appl. No. 14/990,270, filed Jan. 7, 2016. Inventors: Bischoff et al.

* cited by examiner

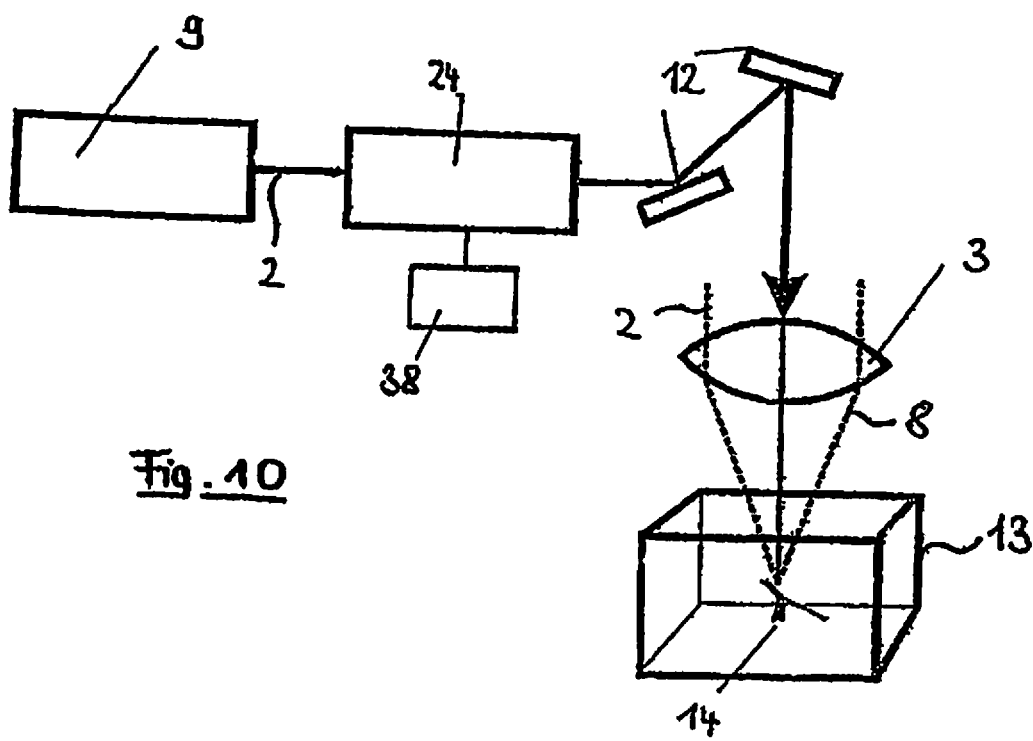
Fig. 10
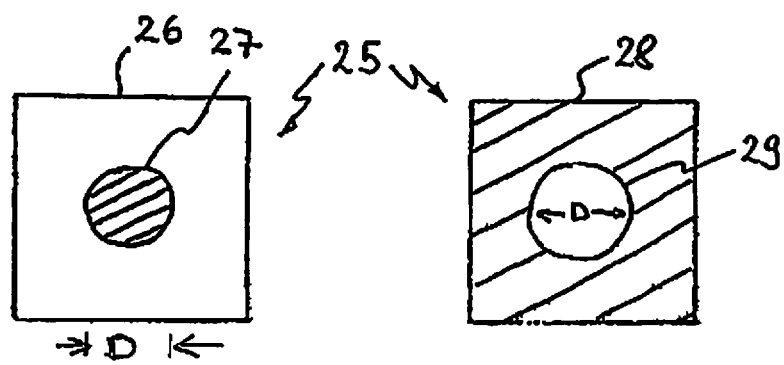
Fig. 11  Fig. 12
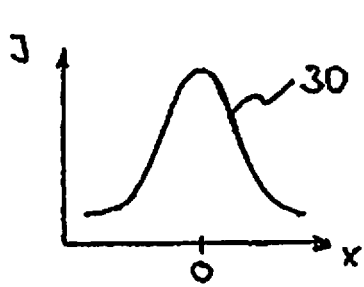 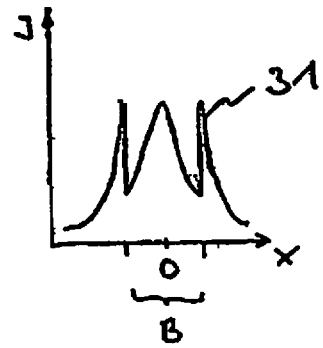
Fig. 13

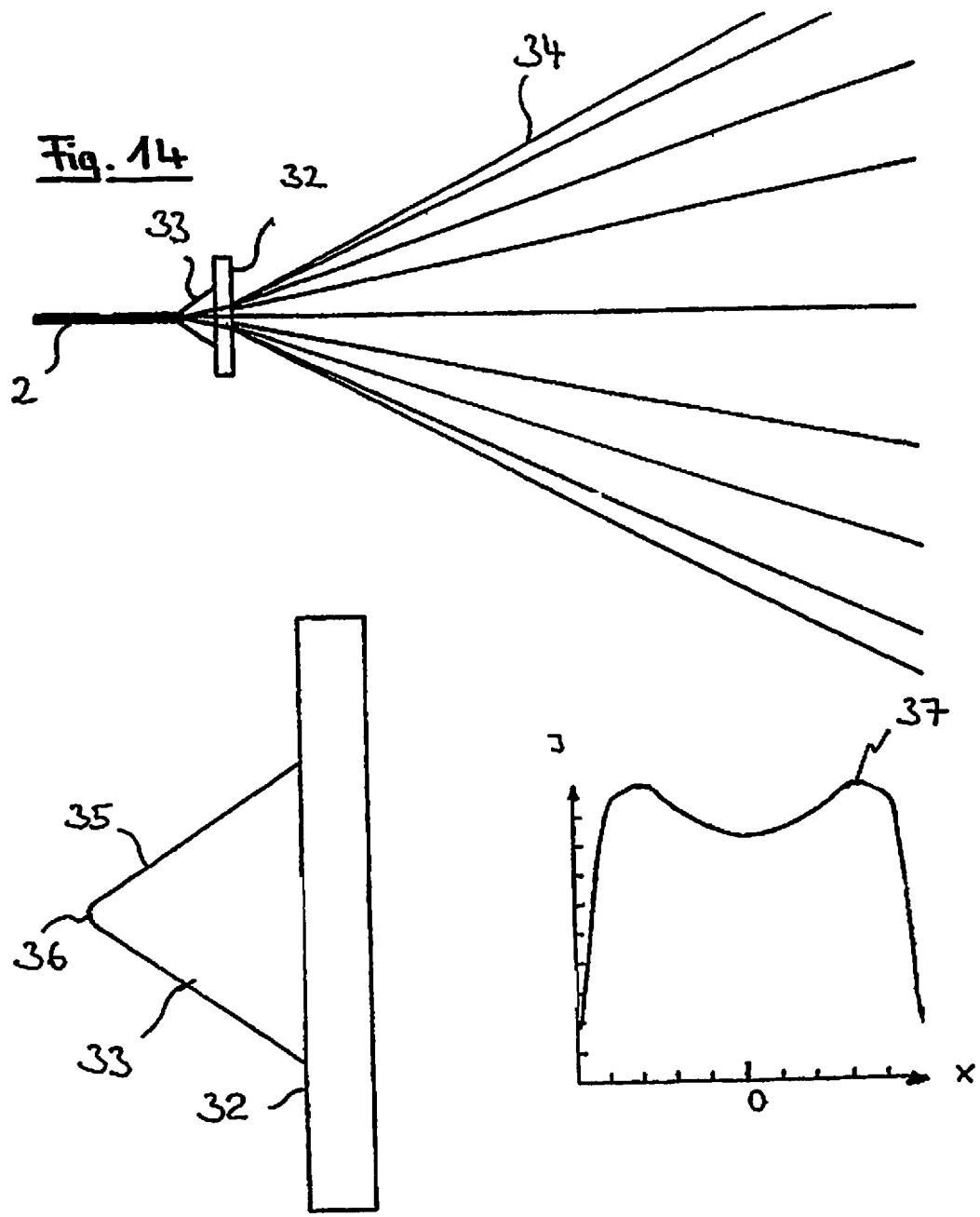

MACHINING DEVICE AND METHOD

RELATED APPLICATIONS

This application is a continuation of application Ser. No. 14/990,270, filed Jan. 7, 2016, entitled Material Machining Device and Method, which is a division of application Ser. No. 10/593,501, filed Sep. 20, 2006, entitled Material Machining Device and Method, now U.S. Pat. No. 9,254,222, issued Feb. 9, 2016, which is a National Stage Entry of PCT/EP2005/003066, filed Mar. 22, 2005, which claims priority to Germany Application DE 10 2004 014 181.9 filed Mar. 23, 2004, all of which are incorporated by reference herein.

FIELD OF THE INVENTION

The invention relates to a machining device which machines a material by non-linear absorption of machining laser radiation and which comprises a laser radiation source emitting laser radiation, and optics focusing said laser radiation for non-linear absorption into or onto the material. The invention further relates to a method of machining, wherein the laser radiation is focused into or onto the material, the parameters of the laser radiation and of focusing being selected such that non-linear absorption of the laser radiation is caused in the material.

BACKGROUND OF THE INVENTION

Laser-based machining is indispensable today in many areas of industrial production. The machining quality achieved by the use of lasers cannot be obtained in many cases by alternative methods. On top of this, high processing speeds are realized in automated production, allowing economically advantageous application of laser-based methods. This can be effected by a multiplicity of complex devices and systems, which are adapted as workstations for a number of specific machining tasks. Industrial workstations comprise, for example, systems for cutting metal sheets as well as devices for machining structures on a microchip. There are also laser systems for carrying out medical processes, for example for correction of eyesight in the case of myopia or hyperopia. These laser systems effect machining of human tissue, while in industrial applications solid materials, such as steel or ceramics, are machined in most cases. Applications for liquid materials, for example laser-assisted polymerization in rapid prototyping, are also important.

If an object is irradiated with laser radiation, this is effected in most cases in order to effect a measurement or in order to machine the material of the object. In each case, there is an interaction between the laser radiation and the material, for example a reflection, a scattering process or an absorption. Important applications in this context are interferometric measuring methods, conventional laser microscopy or exposure of photolacquers in semi-conductor lithography.

However, there are also applications in which conventional, i.e. linear interaction, between the laser radiation and the material is not possible, for example because the material is transparent. In such applications, non-linear interaction between the laser radiation and the material can be utilized for machining, i.e. in particular non-linear absorption of the laser radiation by the material of the object. In this connection, reference is made to $n^{th}$ order absorption, if an absorption of m photons is effected by an atom or a molecule, leading to an n-fold electronic excitation. It has turned out in this case that the likelihood of such $n^{th}$ order absorption depends on the radiation intensity of the laser radiation.

In a transparent material, as it is present, in particular, in laser-surgical ophthalmic methods, several processes initiated by the laser radiation take place one after another in the case of non-linear interaction. If the power density of the radiation exceeds a threshold value, an optical breakthrough is produced in the transparent material, said breakthrough generating a plasma bubble in the material. Due to expanding gases, this plasma bubble grows after the optical breakthrough has formed. If the optical breakthrough is not maintained, for example because pulsed laser radiation has been used, the gas generated in the plasma bubble is re-absorbed by the surrounding material and the bubble disappears. If a plasma is generated at a material boundary surface (which may actually be located within a material structure as well), material removal is effected from said boundary surface. This is then referred to as photoablation, whereas in connection with a plasma bubble separating previously connected material layers one usually speaks of photodisruption. For the sake of simplicity, all such processes are summarized here by the term "optical breakthrough", i.e. this term includes not only the actual optical breakthrough itself, but also the effects resulting therefrom in the material, caused by the non-linear interaction.

High localization of the effect of the laser radiation is required for high-precision machining. Collateral damage in adjacent regions of the material is to be avoided, if possible.

Looking at the probability of non-linear absorption, i.e. multi-photon absorption, it turns out that the probability of such interaction in a laser focus generated by a diffraction-limited optical system is proportional to the $n^{th}$ power of the quotient of laser power times the square of the numerical aperture and the square of the wave length used. For machining at maximum speed by means of non-linear absorption it is desired, of course, to optimize the likelihood of interactions. An increase in such likelihood of multi-photon absorption can be achieved by increasing the laser power, increasing the numerical aperture or decreasing the wave length of use of the laser radiation, as is directly evident from the above-explained context. Therefore, it has been indispensable hitherto in the prior art of non-linearly effective laser machining concepts to use optical systems having a high numerical aperture for focusing.

U.S. Pat. No. 5,894,916 as well as U.S. Pat. No. 6,110,166 describes methods for correcting visual deficiencies by means of suitably generating optical breakthroughs in the human cornea, so that the diffractive properties of the cornea are ultimately influenced in a selective manner. By sequential arrangement of the multiplicity of optical breakthroughs, a lens-shaped partial volume is isolated within the cornea of the eye, said volume then being removed from the cornea by means of a laterally opening cut. The shape of the partial volume is selected such that the diffractive or refractive properties of the cornea are changed after removal of the partial volume to achieve a desired correction of a visual deficiency.

SUMMARY OF THE INVENTION

It is an object of the invention to improve a device for machining by means of laser radiation of the above-mentioned type or a corresponding method of machining, respectively, such that the generation of non-linear interactions is improved.

According to the invention, this object is achieved by a machining device of the above-mentioned type, said device comprising a polarization modulator which causes the focused laser radiation to be linearly polarized, with the direction of polarization varying across the beam cross-section. In an analogous manner, this object is achieved by a method of the above-mentioned type, wherein laser radiation is linearly polarized before focusing, with the direction of polarization varying across the beam-cross section.

Thus, according to the invention, an inhomogeneously polarized field of radiation is used. Although the laser radiation is linearly polarized in each point of the field, it may have a different direction of polarization in each point—in contrast to usual distributions. Surprisingly, the inhomogeneously polarized field of radiation according to the invention leads to a reduction in focus size, thereby increasing the power density in the focus of the laser radiation and thus also the likelihood of initiating multi-photon processes. Previously, said focus reduction had only been assumed theoretically (Quabis et al., Opt. Com., 179, 2000) or discussed experimentally for optical data storage, respectively (Dorn et al., J. Mod. Opt. 50, 12, p. 1917-1926, 2003). Surprisingly, the concept of continuous wave radiation (cw radiation) discussed throughout the prior art for linear interaction can also be advantageously used for non-linear interactions, and in particular when using pulsed laser radiation. For example, in the case of the above-described machining by means of optical breakthroughs the energy transmitted into the material can now be minimized, thus keeping collateral damage low. If several optical breakthroughs are sequentially arranged by the concept according to the invention in order to effect areal material separations, an improved quality of cutting is achieved due to the reduced focus obtained according to the invention.

The object is further achieved by a machining device of the above-mentioned type, which device comprises an intensity modulator modifying an intensity distribution of the laser radiation while attenuating the radiation intensity near the optical axis. In an analogous manner, the object is achieved by a method of the above-mentioned type, wherein the intensity distribution of the laser radiation is modified prior to focusing, while the radiation intensity near the optical axis is being attenuated.

Thus, the polarization modulator and the intensity modulator can be used alternatively in order to achieve the object of the invention. The intensity modulator causes a suitable change in the beam profile. The inventors have found that a beam profile modification reducing the radiation intensity near the optical axis surprisingly also leads to a reduced focus size, i.e. to better focusing. Since conventional sources of laser radiation usually emit a laser beam having a Gauss-shaped profile, the intensity modulator for such machining devices has the effect that regions viewed along the beam profile, located far from the optical axis, bear a proportionally higher percentage of intensity than in the Gauss-shaped profile.

In a simple design of the intensity modulator, it blocks out these radiation components near the optical axis or attenuates them. Possibilities to realize this exist, for example, in the shape of a point-shaped stop or a punctiform absorbing unit located at the center of the beam-cross section, or of a reflector deflecting the beam path, which reflector, located at the center, reflects poorly or not at all. Any power losses connected therewith throughout the cross-section of the laser radiation can be compensated for by suitably increasing the radiation power preceding the intensity modulator.

If it is desired to leave the radiation power of the laser radiation unchanged, if possible, an intensity modulator is suitable which effects a re-distribution of energy in the beam cross-section, wherein energy is distributed away from regions located near the optical axes toward outer regions of the beam cross-section. An example of the optical principles which an intensity modulator acting in this way has to comply with is found, for example in U.S. Pat. No. 4,826,299, the disclosure of which, in particular with respect to the optical parameters of FIG. 16 therein, is explicitly incorporated herein by reference.

The use of non-Gauss-shaped laser radiation and in particular laser radiation having low intensity at the center of the laser beam is quite a surprising result considering the fact that the optical quality of objectives used for focusing is usually much better near the optical axis than in regions remote from the axis. It is a well-established fact in the prior art that, in order to increase the quality of the focus, the radiation should be guided, if possible, near the optical axis, because radiation guided in regions remote from the axis usually leads to an astigmatism of the image.

The above-mentioned intensity modulation can be used as an alternative or in addition to the aforementioned polarization modulation. Thus, where general reference is made hereinafter to modulation or to a modulator, respectively, this may mean both intensity modulation and polarization modulation. It is also possible to connect effects of polarization and of radiation intensity via the beam-cross section in a mutually adapted manner.

A further surprising advantage of the invention shows in the inventive procedure in combination with multi-dimensional shifting of the focus position, because the excellent quality of focus achieved by the invention otherwise required very large numerical apertures in the prior art, which apertures were a hindrance to a large area of deflection for the focus but can now be smaller.

The inventors realized that using the approach according to the invention in presently already realized optical systems for machining in connection with refractive eye surgery by means of femtosecond laser radiation, a reduction of the focus diameter by up to 30% is achieved. This reduces the radiation exposure by up to 50% when generating a single optical breakthrough, or if the radiation load associated with machining is kept constant, a duplication of the repetition frequency of the pulsed laser radiation and thus a fifty percent reduction of the total machining time can be achieved.

Thus, according to the invention, an increase in energy or power density, respectively, in the laser focus for machining by laser is realized by providing
  a laser radiation source,
  the optical module referred to as a modulator,
  preferably a deflecting unit which controls the spatial position of the focus of the laser radiation with respect to the material by influencing the direction and/or divergence of the laser beam, and
  an objective which is designed such that it is adapted for focusing the laser radiation into the material in order to achieve efficient non-linear absorption of the laser radiation in the material.

The laser radiation interacting non-linearly with the material is preferably pulsed and has a high peak power, as is the case for example with femtosecond laser radiation. The modulator, which is a polarization modulator in one embodiment, uses one or several structural components for converting homogeneously linearly polarized laser radiation, such as that which is usually emitted by laser radiation sources, to inhomogeneously linearly polarized laser light.

In order to produce a cut surface, multi-dimensional shifting of the focus in or on the material is conveniently effected, as already mentioned. Therefore, a further embodiment is preferred which comprises a deflecting unit modifying a spatial position of the focus in or on the material by controllable deflection of the laser radiation.

What is essential in achieving the superior focus quality according to the invention is the polarization direction varying across the beam cross-section of the linearly polarized laser radiation and the reduced radiation intensity near the optical axis. Therefore, for a particularly easy to realize construction, the modulator will be arranged following the laser radiation source and, in the case of further embodiments comprising a deflecting unit, will be arranged between the laser radiation source and the deflecting unit. The modulator is advantageously located in any pupil plane of the beam path between the laser radiation source and the material to be machined. The position of the intensity modulator is not fixed and can be adapted to an application by means of a propagation calculator. In a special case which is particularly easy to understand, the modulation plane and the focal plane are conjugated; the beam profile in the focus then corresponds directly to the Fourier-transformed beam profile following the modulator.

As an alternative to the modulator subsequently modulating homogeneously linearly polarized or Gauss-shaped laser radiation, the polarization modulator or the intensity modulator can also be arranged directly in the laser radiation source, so that the latter already emits laser radiation having a polarization direction which varies over the beam cross-section or having a non-Gauss-shaped intensity distribution.

It has been shown that, according to the geometry of the beam path by which the laser radiation is focused into or onto the material and depending on the material, different forms of inhomogeneously linearly polarized laser radiation or laser radiation differing in the intensity distribution within the profile may be preferred. In terms of universal usability of the machining device or applicability of the machining method it is convenient if the modulator is adjustable or in particular controllable so as to vary the polarization direction or to change the intensity distribution. Adjustment can be conveniently effected during operation of the device, for example by intervention of a corresponding control unit.

Using a controllable modulator, quality control of machining can advantageously be effected such that a measured value determined during machining, for example a quality parameter, is suitably controlled using the variation of the polarization directions or the change in intensity distribution as manipulated variables.

The concept according to the invention is surprisingly advantageous where pulsed laser radiation having a very short pulse duration is used, thus making more efficient use of the energy introduced into the material for machining. It is therefore preferred that the laser radiation source emit pulsed laser radiation having a pulse duration of less than 10,000 fs, in particular less than 500 fs. A particularly optimal value in the field of ophthalmic surgery has turned out to be approximately 350 fs. If the pulses are even shorter, the increasing spectral width of the pulses increases the technical complexity.

The inhomogeneously linearly polarized laser radiation used according to the invention further enables rapid machining; for example, in the case of pulsed laser radiation, a pulse repetition frequency of over 100 kHz, in particular of over 450 kHz, is possible.

For non-linear interaction of the laser radiation with the material, focusing may be effected, on the one hand, into the material, i.e. below its surface. However, it is also possible to focus the laser radiation in the vicinity of the surface of the material to be machined. A particularly good photoablative effect is achieved if the distance of the laser focus from the surface of the material to be machined is approximately within the range of the Rayleigh length of laser radiation.

The laser radiation to be used according to the invention is particularly convenient if, in particular by areal sequential arrangement of optical breakthroughs in the material, cut surfaces are formed which are located in the material and may have a cutting line extending up to the surface of the material.

BRIEF DESCRIPTION OF THE DRAWINGS

The invention will be explained in more detail below, by way of example and with reference to the drawings, wherein:

FIG. 10 shows a schematic view of a second embodiment of a laser machining device similar to FIG. 4;

FIGS. 11 and 12 show different variants of a structural component which may be used in the laser machining device of FIG. 10;

FIG. 13 shows beam profiles which are possible in the laser machining device of FIG. 10;

FIG. 14 is a schematic drawing illustrating a further variant of the structural element of FIGS. 11 and 12;

FIG. 15 is a sectional view of the structural element of FIG. 14, and

FIG. 16 is a beam profile obtainable with the structural component of FIG. 15.

DETAILED DESCRIPTION

Figure 1:
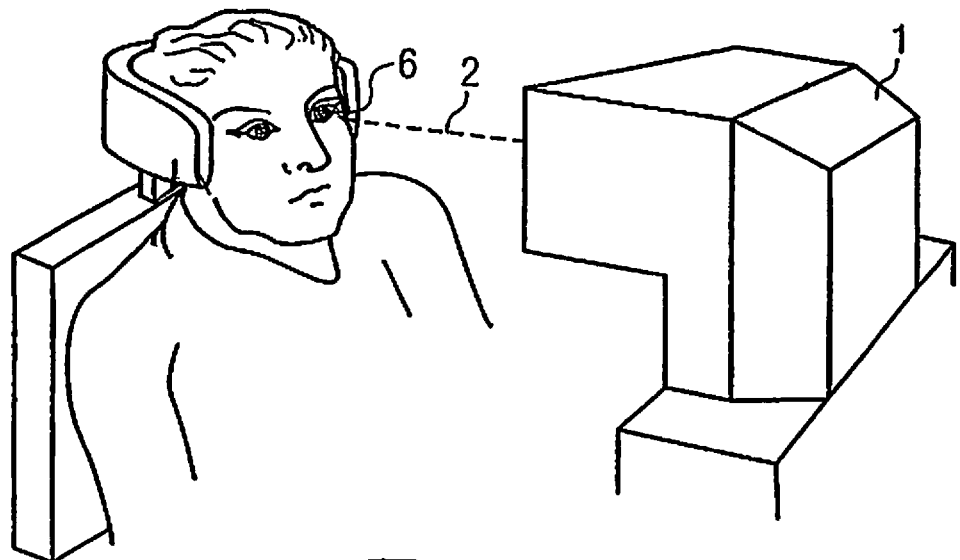
FIG. 1 shows a perspective view of a patient during laser-surgical treatment using a laser-surgical instrument.

FIG. 1 shows a laser-surgical instrument 1 emitting a treatment beam 2 which is directed onto the eye 6 of a patient. The laser-surgical instrument 1 generates a pulsed treatment beam 2 such that the method described in U.S. Pat. No. 6,110,166 can be carried out. The pulsed duration is in the nano- or femtosecond range.

Using the laser-surgical instrument 1 a visual deficiency of the eye 6 of the patient is remedied by removing material from the cornea such that the diffractive characteristic of the cornea is changed to a desired extent. In doing so, material is removed from the stroma of the cornea, said stroma being located below the epithelium and the Bowman membrane as well as above the Decemet membrane and the endothelium.

The laser-surgical instrument 1 machines a material which is actually transparent to laser radiation. The pulsed laser radiation of the treatment beam 2 is therefore irradiated such that non-linear absorption occurs in order to generate the optical breakthrough.

Material removal is achieved by focusing the high-energy pulsed treatment beam 2 of the laser-surgical instrument 1 into the stroma, thereby generating optical breakthroughs. Each single optical breakthrough initiates a plasma bubble so that tissue is separated. By suitable deflection of the treatment beam 2, plasma bubbles are sequentially arranged during treatment, which bubbles then circumscribe a partial volume of the stroma, namely the material to be removed. Due to the treatment beam 2, the laser-surgical instrument 1 acts like a surgical knife which, without injuring the surface of the cornea, cuts material directly within the transparent cornea of the eye. If the cut is guided up to the surface of the cornea by further generating optical breakthroughs, the material of the stroma isolated by the cut profile can be pulled out laterally and removed from the cornea.

Figure 2:
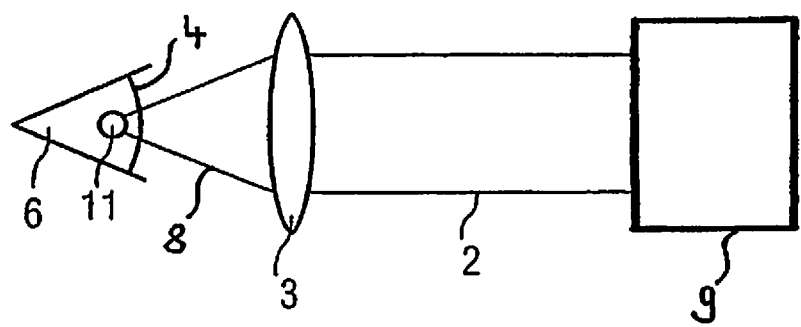
FIG. 2 shows a schematic view of the focusing of a ray bundle onto the patient's eye with the instrument of FIG. 1.

As shown in FIG. 2, the laser-surgical instrument 2 comprises a laser source 9 whose treatment beam 2 is focused as focused laser radiation 8 into the cornea 4 of the eye 6 by means of an (adjustable) objective 3. The already mentioned plasma bubble 11 is then formed in the focus.

Figure 3:
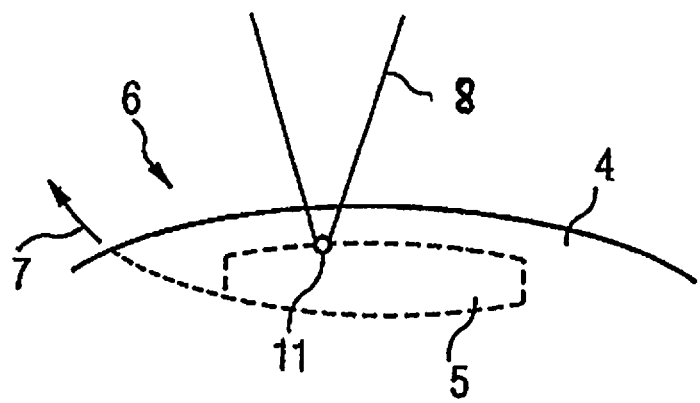
FIG. 3 shows a schematic view illustrating the cut path effected during laser-surgical treatment.

FIG. 3 schematically shows how a cut surface is generated in the cornea 4 in order to isolate a partial volume 5. By suitable three-dimensional shifting of the focused laser beam 8, many plasma bubbles 11 are sequentially arranged in order to form a cut surface (shown in broken lines in FIG. 3). If the partial volume 5 is isolated within the cornea 4, the cut is guided up to the periphery such that material of the partial volume 5 can be pulled out in the direction of the arrow 7.

Figure 4:
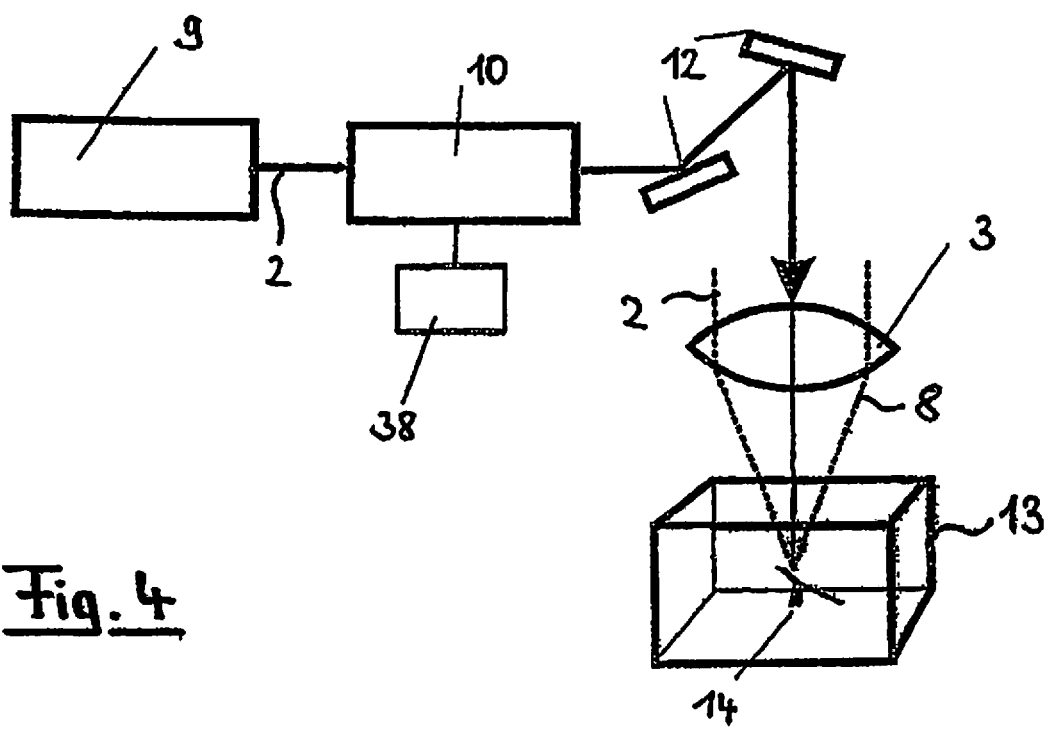
FIG. 4 shows a schematic view of a first embodiment of a laser machining device for generating wave guide structures.

The structure of a laser treatment instrument is shown in simplified form in FIG. 4 for a first embodiment, said instrument being substantially similar to the laser-surgical instrument 1, but in this case serving to form a wave guide structure 14 in a transparent material 13. A polarization modulator 10 (which, although not mentioned, is also provided in the beam path of the laser-surgical instrument 1) is arranged following the laser source 9 said polarization modulator modifying the linearly polarized radiation 2 emitted by the laser source 9 such that it has inhomogeneous linear polarization conditions.

The inhomogeneous linear polarization conditions are characterized in that the polarization vector $\vec{P}$ of the field does not have a uniform direction across the cross-section of the collimated laser beam.

For physical characterization of such polarization conditions it should be noted first that for a collimated laser beam the field strength can be approximated conventionally as a planar wave. The position of the field strength vector can then be represented for linearly polarized light in any x, y coordinate system in which the wave propagates in the direction of z:

$$\vec{E} = \{E_{0x}, E_{0y}\} \exp_{i(\omega t - kz)}$$

For simplification, the standardized polarization vector $\vec{P}$ of the field can now be introduced, the amplitude of the field strength being determined completely by the amplitude function $\sqrt{E_{0x}^2 + E_{0y}^2}$. Although said amplitude function drops rapidly for a Gauss beam, the following equation applies to the polarization vector, regardless of the specific amplitude distribution:

$$\vec{P} \equiv \frac{E_{0x}\vec{e}_x + E_{0y}\vec{e}_y}{\sqrt{E_{0x}^2 + E_{0y}^2}}$$

Thus, the field strength results as:

$$\vec{E} = \sqrt{E_{0x}^2 + E_{0y}^2} \cdot \vec{P} \cdot \exp i(wt - kz)$$

The polarization vector is a function of x and y. If $$\vec{P} = \vec{P}_{(x,y)=\text{const.}}$$

then this is a homogeneously linearly polarized field such as that which is emitted by most lasers, for example by a helium-neon laser. If $$\vec{P} = \vec{P}_{(x,y)\neq\text{const.}}$$

then the corresponding field of radiation is inhomogeneously linearly polarized.

After an inhomogeneously linear polarization has thus been imposed on the laser radiation 2, the latter passes through a deflecting unit 12, which is symbolized here in the form of two deflecting mirrors being independently tiltable about orthogonal axes. Together with the adjustable objective 3, the focused laser beam 8 can thus be three-dimensionally shifted within the volume of the transparent material 13, thus allowing to form three-dimensional structures in the material, for example the wave guide structure 14 as shown. The pulsed laser radiation 2 emitted by the radiation source 9 is non-linearly absorbed by the material 13, thus causing a permanent change in material properties within the spatial region machined. As an alternative or in addition to the effect of the deflecting unit 12 and the adjustable objective 13, it is certainly also possible to move the object with the transparent material 13 itself relative to the objective 3. This may be of interest in particular if structures are to be generated whose extent goes at least partially beyond the positions achievable by the deflecting unit 12 or the length of adjustment of the objective 3.

Due to the inhomogeneously linear polarization of the focused laser beam 8, a focus is obtained in the transparent material 13, which focus has smaller dimensions than would actually expected due to the beam path and in particular due to the objective 3. The precision of machining is thus increased. The same goes for the instrument 1 of FIG. 1.

The focus reduction achieved by the polarization modulator 10 may differ according to the beam path and in particular according to the type of transparent material 13. For optimization, it is therefore conveniently envisaged that the quality of machining, for example the size of the spatial region in which a non-linear interaction is determined, is measured and an optimization is effected by varying the setting of the polarization modulator 10. For example, the size of a plasma bubble generated in the material 13 or in the cornea 4 can be measured and minimization can be effected by adjusting the polarization modulator 10 which is controlled by a control device (not shown). Alternatively, the radiation emitted by the laser source 9 can also be gradually reduced by suitable control of the polarization modulator 10 until a minimal radiation power or pulse duration is present which is still sufficient for the desired non-linear interaction.

Figure 5:
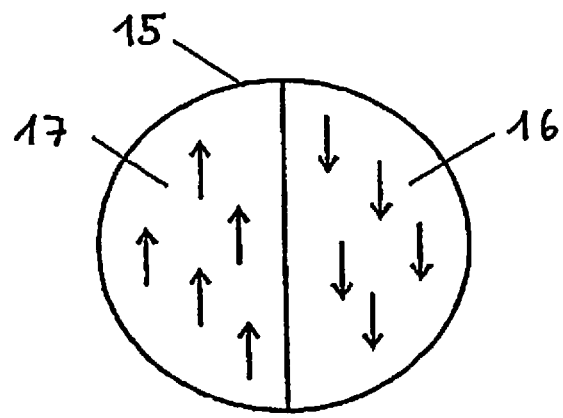
FIG. 5 shows an example of inhomogeneously linear polarization of a laser beam according to the first embodiment comprising sectorial polarization variation.

The effect of the polarization modulator 10 is shown by way of example in FIG. 5, showing an x-y section 15 through the laser beam 2 which propagates in the direction of z (perpendicular to the drawing plane). As can be seen, the polarization modulator 10 imparts to the laser beam 2 an inhomogeneous polarization distribution in such a form that two partial regions 16 and 17 are present in which the polarization direction, although being respectively identical, has a phase shift of 180° with respect to the other partial region. This is symbolized in FIG. 5 by the arrows which are parallel, but point in opposite directions. Instead of an inhomogeneity comprising two partial regions 16 and 17, it is also possible, of course, to use any other sectorial polarization.

Figure 6:
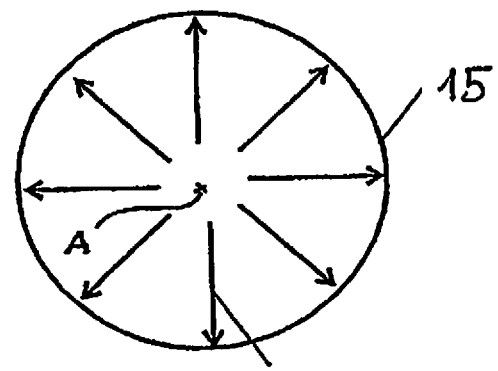
FIG. 6 shows a further example of inhomogeneously linear polarization of a laser beam according to the first embodiment with radial polarization variation.

FIG. 6 shows a radial polarization distribution in the x-y section 15. The polarization directions point radially outwardly from the optical axis A.

Figure 7:
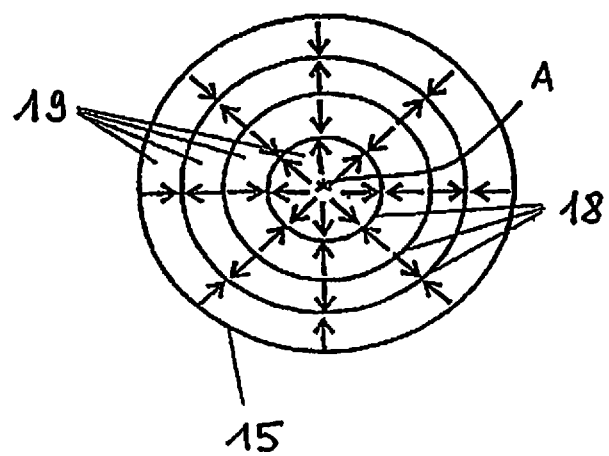
FIG. 7 shows a further example of inhomogeneously linear polarization of a laser beam according to the first embodiment with discontinuous radial polarization variation.

FIG. 7 shows an inhomogeneous polarization comprising phase jumps within annular portions in the x-y section 15. The phase jumps appear at jump locations 18 concentrically arranged about the optical axis A. The laser beam 2 is divided into four rings 19 having different polarization, as viewed in the x-y section 15. Between adjacent rings there is a phase jump of the polarization direction, which jump is shown as an 180° phase jump for reasons of illustration. Of course, any other phase jump is also possible.

In order to form one of the inhomogeneous linear polarization conditions of FIGS. 5 to 7 the polarization modulator 10 according to a preferred alternative embodiment comprises a segmented wave plate which causes the desired polarization modulation alone or in combination with other optical components. In a further alternative embodiment, dichroic glass polarizations are provided which are designed according to the desired polarization distribution for the respective application. Also, liquid crystal components can be used, which are usually referred to as spatial light modulators (SLM) and enable flexible adaptation of the polarization distribution to a respective processing task, controlled by a corresponding adjusting signal.

Figure 8:
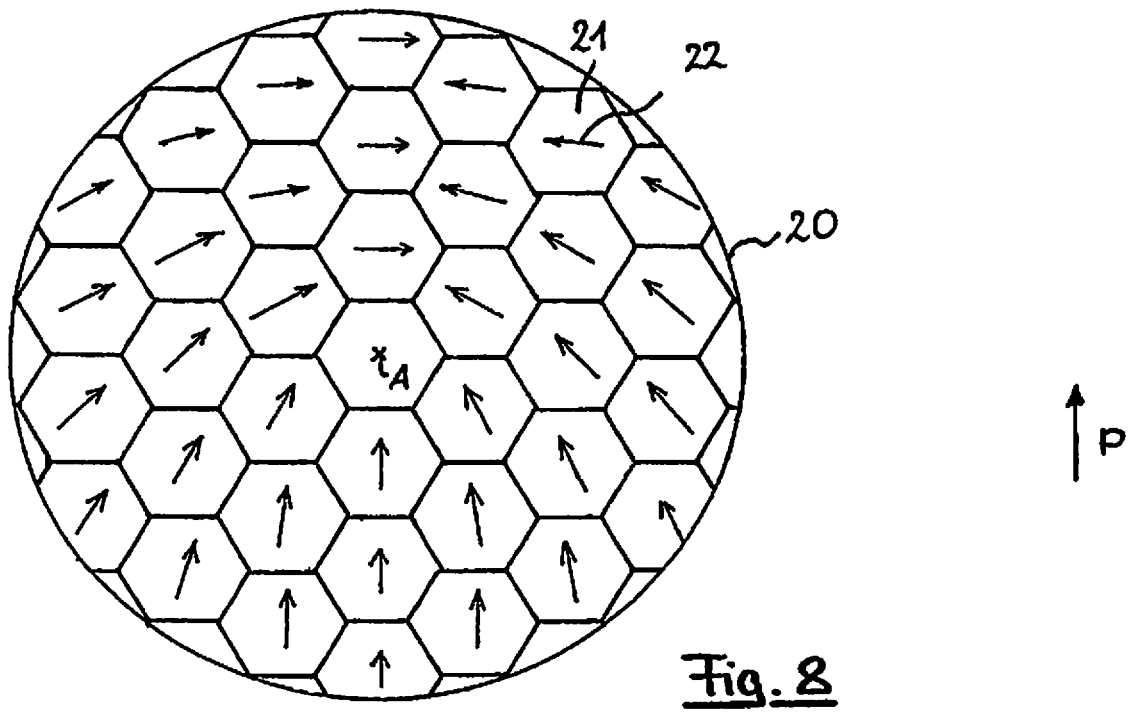
FIG. 8 shows a top view of a polarization modulator of the first embodiment for generating processing laser radiation with inhomogenously linear polarization.

FIG. 8 shows a further possible design of a polarization modulator 10 as known for a completely different application from EP 0,764,858 A2, whose disclosure is fully incorporated herein by reference. It refers to a honeycomb condenser 20 comprising a multiplicity of honeycomb-shaped cells 21. The cross-section of the laser beam 2 is thus divided into a multiplicity of facets 21. Each facet 21 consist of a half-wave plate of birefringent material and is oriented, for example, according to the pattern shown in FIG. 8. Therefore, they are each oriented in the direction of the angle bisector between the polarization direction P, also shown in FIG. 8, of the incident linearly polarized laser radiation 2 and the respective radius, oriented towards the optical axis A, through the center of each facets 21. Thus, each half-wave plate facet 21 effects rotation of the polarization direction in the direction of the aforementioned radius.

Figure 9:
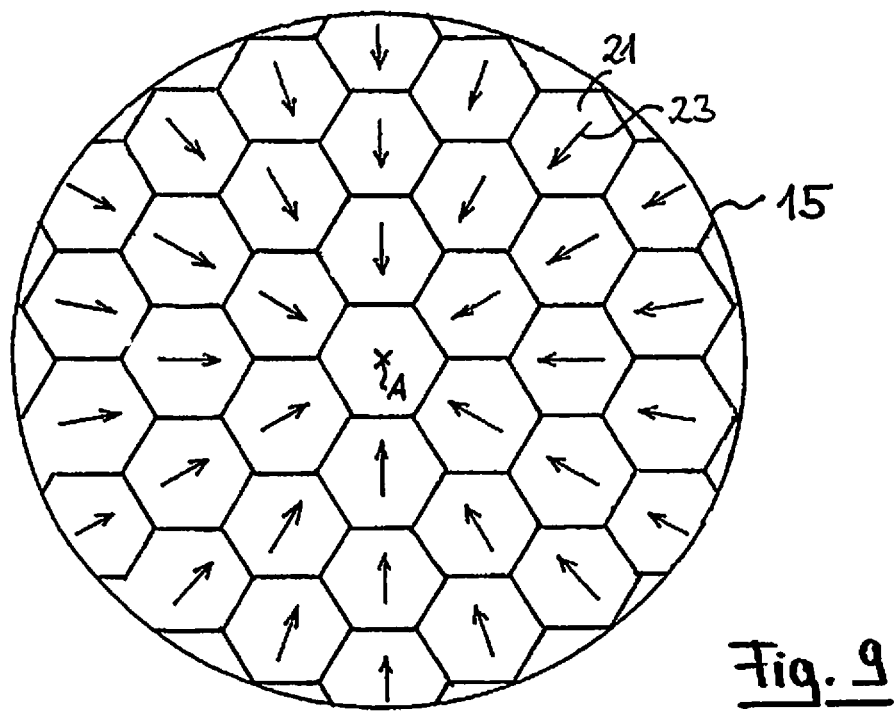
FIG. 9 shows the polarization directions of the laser radiation upon application of the polarization modulator of FIG. 8.

FIG. 9 shows the effect of this arrangement of the main axes 22 of the facets 21 of the honeycomb condenser 20, due to the polarization directions 23 being radially aligned with the optical axis A after passage.

FIG. 10 is a simplified view of a second embodiment of a design for a laser processing instrument 1 which is essentially similar to that of FIG. 4. The difference in design concerns the modulator arranged following the laser source 9, which modulator is provided as an intensity modulator 24 here. The remaining elements correspond to those already explained for the first embodiment, so that their description is not repeated here.

The intensity modulator 24 modifies the beam profile of the treatment beam 2 such that the radiation intensity near the optical axis is attenuated. Therefore, the intensity modulator 24 is located in a plane conjugated with the focal plane in the construction shown in FIG. 10. The intensity modulator 24 employs a modulating element 25 for which two possible constructions are shown in FIGS. 11 and 12.

The element 25 in the construction of FIG. 11 is formed from a transparent substrate 26 onto which a circular stop element 27 is applied here. The stop element 27 has a diameter D, which covers, for example, 50% of the beam cross-section of the treatment beam 2. Instead of a covering stop element 27 use can also be made of an absorbing element 27 attenuating, but not shading, the treatment laser beam 2 in the core region indicated by hatching.

The same result is obtained with the construction of the element 25 shown in FIG. 12; however, this variant 27 works reflectively. For this purpose, a mirror coating 28 is provided, which is transparent or partially transparent in a circular region 29 within the beam cross-section.

Those radiation components passing through the region 29 are separated from the treatment beam 2 and only the reflected components are bundled in the focus. Instead of being fully transparent, the circular region 29 may also be partially reflective, which again results in attenuation in the core region of the treatment laser beam 2.

An exemplary result for the beam profile obtainable with the element 25 is shown in FIG. 13. The initially Gauss-shaped profile 30, plotted as the intensity I against the location x in the left-hand graph of FIG. 13, is deformed by the effect of the intensity modulator 24 to a profile 31 which is considerably attenuated at the center with a diameter B. It should be noted that the illustrations of the left-hand graph and the right-hand graph of FIG. 13 do not have the same scale on the intensity axis; the right-hand graph is enlarged in terms of intensity so as to make the effect clear.

As a result, the treatment beam 2 is no longer Gauss-shaped in profile after the intensity modulator 24, which likewise leads to an improved quality of focus as does the polarization modulation already explained with respect to the first embodiment.

A further possibility of realizing the intensity modulator 24 is shown in FIGS. 14-16. In this case, a Powell asphere 33 is provided on a substrate 32 in the intensity modulator 24, which asphere spreads the treatment beam 2 with a Gauss-shaped profile out in a certain manner such that a diverging ray bundle 34 forms. As the representation of exemplary partial beams in FIG. 14 clearly shows, the Powell asphere 33 causes an energy re-distribution away from the optical axis. Following a converging lens (not shown in FIG. 14 for simplification) and/or a diffractive optical element, the treatment beam 2 is then present with a non-Gauss-shaped profile. An example of the achievable profile is shown in FIG. 16. As can be seen, the intensity I of the modified treatment beam 2 is distributed in a near-rectangular profile 37 across the beam cross-section.

The effect of the Powell asphere 33 is primarily due to its cone shape, as viewed in cross-section. FIG. 15 shows this cone 35. The point of the cone 35 is rounded off at a certain radius 36. Details concerning the construction and design of the Powell asphere 33 are found in the already mentioned U.S. Pat. No. 4,826,299.

In a further advanced embodiment, the instrument 1 may use both a polarization modulator 10 according to one of the described constructions and an intensity modulator 24 in one of the described constructions. Conveniently, the polarization modulator may also realize an amplitude modulation at the same time. For this purpose, the rings 19 of FIG. 7 or the cells of facets 21 of FIG. 8 may be provided, for example, with suitable radiation intensity-influencing properties, so that the radiation intensity at the center of the beam is attenuated. A combination of the polarization modulator 10 with the intensity modulator 24 in one component leads to a particularly compact design. A combination of a separate polarization modulator 10 with an individual intensity modulator 24, on the other hand, can be realized at comparatively low cost.

The invention claimed is:

1. A machining device configured to machine a material by non-linear absorption of
 machining pulsed laser radiation, the device comprising:
  a pulsed laser radiation source emitting a beam of pulsed laser radiation, the beam having a gauss-shaped beam cross-section when emitted from the pulsed laser radiation source,
  focusing optics configured to focus the beam for non-linear absorption into or onto the material to generate multiphoton interaction between the laser radiation and the material; and
  a modulator which is located in a beam path before the focusing optics and which modifies a distribution of an optical parameter of intensity or polarization across the gauss-shaped beam cross-section resulting in the focusing optics producing a first focus size reduced below a second focus size, the second focus size being that which the focusing optics would generate without the modulator.

2. The machining device as claimed in claim 1, wherein the optical parameter modified is intensity and the modulator comprises an intensity modulator that attenuates beam intensity near an optical axis of the focusing optics.

3. The machining device as claimed in claim 2, wherein the intensity modulator blocks out beam components near an optical axis of the focusing optics.

4. The machining device as claimed in claim 2, wherein the intensity modulator redistributes energy over the beam cross-section to remove energy from regions near an optical axis of the focusing optics.

5. The machining device as claimed in claim 2, wherein the intensity modulator is adjustable, with respect to the modification of the distribution of intensity over the beam cross-section.

6. The machining device as claimed in claim 2, wherein the intensity modulator is adjustable, with respect to the variation of the optical parameter over the beam cross-section, and wherein the machining device further comprises a control unit which adjusts the variation of the optical parameter during operation of the machining device.

7. The machining device as claimed in claim 1, wherein the optical parameter is polarization and the modulator comprises a polarization modulator introducing a polarization which varies across the beam cross-section.

8. The machining device as claimed in claim 7, wherein the modulator is adjustable, with respect to the modification of the distribution of polarization over the beam cross-section.

9. The machining device as claimed in claim 7, wherein the polarization modulator is adjustable, with respect to the variation of the optical parameter over the beam cross-section, and wherein the machining device further comprises a control unit which adjusts the variation of the optical parameter during operation of the machining device.

10. The machining device as claimed in claim 1, further comprising a scanner which modifies a spatial position of the focus in or on the material.

11. The machining device as claimed in claim 10, wherein the modulator is arranged between the laser radiation source and the scanner.

12. The machining device as claimed in claim 1, wherein the modulator is included in the laser radiation source.

13. The machining device as claimed in claim 12, wherein the pulse repetition frequency is above 450 kHz.

14. The machining device as claimed in claim 1, wherein the laser radiation source emits pulsed laser radiation with a pulse duration of less than 10,000 fs.

15. The machining device as claimed in claim 14, wherein the pulse duration is less than 500 fs.

16. The machining device as claimed in claim 1, wherein the laser radiation source operates at a pulse repetition frequency of more than 100 kHz.

17. The machining device as claimed in claim 1, wherein the focusing optics is further configured to focus the beam to a vicinity of a surface of the material to be machined, with a distance of the focus from the surface lying approximately in a range of the Rayleigh length of the radiation.

18. A method for machining a material, comprising:
 providing a pulsed laser beam of gauss-shaped beam cross-section,
 utilizing focusing optics to focus the beam into or onto the material;
 modifying, before focusing, a distribution of an optical parameter of intensity or polarization across the beam cross-section resulting in the focusing optics producing a first focus size reduced below a second focus size, the second focus size being that which the focusing optics would generate without the modifying; and
 selecting parameters of the laser radiation, the modifying and the focusing such that a non-linear absorption with multiphoton interaction between the laser radiation and the material occurs.

19. The method as claimed in claim 18, wherein the optical parameter is intensity and further comprising modifying to attenuate beam intensity near an optical axis of the focusing optics.

20. The method as claimed in claim 19, wherein the modifying comprises blocking out beam components near the optical axis.

21. The method as claimed in claim 19, wherein the modifying further comprising redistributing energy over the beam cross-section to remove energy from regions near an optical axis of the focusing optics.

22. The method as claimed in claim 18, wherein the optical parameter is polarization and the modifying further comprises introducing a polarization which varies across the beam cross-section.

23. The method as claimed in claim 18, wherein the modifying further comprises adjusting the distribution of intensity or polarization during machining.

24. The method as claimed in claim 23, further comprising closed-loop controlling a quality parameter of machining, with variation of distribution of the parameter of the intensity or polarization being used as a manipulated variable in the closed-loop control.

25. The method as claimed in claim 18, further comprising shifting a spatial position of the focus in or on the material at least two-dimensionally.

26. The method as claimed in claim 18, further comprising emitting the pulsed laser beam to have a pulse duration of less than 10,000 fs.

27. The method as claimed in claim 26, further comprising emitting the pulsed laser beam to have the pulse duration less than 500 fs.

28. The method as claimed in claim 18, further comprising emitting the pulsed laser beam to have a pulse repetition frequency of more than 100 kHz.

29. The method as claimed in claim 28, further comprising emitting the pulsed laser beam to have the pulse repetition frequency above 450 kHz.

30. The method as claimed in claim 18, the focusing further comprising focusing the beam to a vicinity of a surface of the material to be machined, with a distance of the focus from the surface lying approximately in the range of the Rayleigh length of the radiation.

31. The method as claimed in claim 18, further comprising forming at least one cut surface in the material by sequential arrangement of optical breakthroughs generated by the non-linear absorption.

32. The method as claimed in claim 31, further comprising forming the cut surfaces to be located in the material and to have a cutting line extending up to a surface of the material.

* * * * *